(12) United States Patent
Sitka et al.

(10) Patent No.: US 6,349,373 B2
(45) Date of Patent: *Feb. 19, 2002

(54) DIGITAL IMAGE MANAGEMENT SYSTEM HAVING METHOD FOR MANAGING IMAGES ACCORDING TO IMAGE GROUPS

(75) Inventors: Larry R. Sitka, Stillwater; Dean P. Beilke, Apple Valley, both of MN (US)

(73) Assignee: Eastman Kodak Company, Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/026,986

(22) Filed: Feb. 20, 1998

(51) Int. Cl.[7] .............................................. G06F 12/16
(52) U.S. Cl. .......................... 711/161; 707/204; 705/2; 705/3
(58) Field of Search ................................ 711/117, 161, 711/162; 707/204; 705/2, 3

(56) References Cited

U.S. PATENT DOCUMENTS

| | | | | |
|---|---|---|---|---|
| 3,872,448 A | * | 3/1975 | Mitchell, Jr. ..................... | 705/3 |
| 4,833,625 A | | 5/1989 | Fisher et al. ................. | 345/439 |
| 4,897,802 A | * | 1/1990 | Atkinson et al. ............. | 40/362 |
| 5,027,110 A | | 6/1991 | Chang et al. ................ | 345/131 |
| 5,140,518 A | | 8/1992 | Ema ........................... | 600/300 |
| 5,276,867 A | * | 1/1994 | Kenley et al. ............... | 707/204 |
| 5,297,034 A | | 3/1994 | Weinstein .................... | 382/128 |
| 5,374,965 A | | 12/1994 | Kanno ........................ | 348/705 |
| 5,410,676 A | | 4/1995 | Huang et al. ................ | 711/202 |
| 5,437,024 A | | 7/1995 | French ........................ | 707/10 |
| 5,469,353 A | | 11/1995 | Pinsky et al. ............... | 382/131 |
| 5,471,606 A | | 11/1995 | Huang et al. .......... | 395/500.45 |
| 5,499,626 A | | 3/1996 | Willham et al. ............ | 600/300 |
| 5,502,576 A | | 3/1996 | Ramsay et al. ............. | 358/444 |
| 5,513,101 A | | 4/1996 | Pinsky et al. ................. | 705/3 |
| 5,600,574 A | | 2/1997 | Reitan ........................ | 702/185 |
| 5,642,513 A | | 6/1997 | Schnellinger et al. ....... | 395/705 |
| 5,764,972 A | * | 6/1998 | Crouse et al. ................ | 707/1 |
| 5,842,222 A | * | 11/1998 | Lin et al. .................... | 707/202 |
| 6,012,093 A | * | 1/2000 | Maddalozzo, Jr. et al. . | 709/223 |
| 6,023,710 A | * | 2/2000 | Steiner et al. .............. | 707/204 |

\* cited by examiner

Primary Examiner—Matthew Kim
Assistant Examiner—Matthew D. Anderson
(74) Attorney, Agent, or Firm—William F. Noval

(57) ABSTRACT

A digital image management system is described which facilitates image archival with a unique method for grouping customer images and information. As applied to medical environments, the system creates a virtual film jacket and implements the unique method by modeling convention hospital film archival procedures. The invention facilitates archival to a variety of devices including a redundant array of independent disks, magneto-optical storage devices and digital linear tapes and eliminates the need for hospital staff to retrieve several tapes from archive in order for a radiologist to review a patient's study. The invention is applicable to any environment where customer images and information are continuously archived and retrieved.

24 Claims, 5 Drawing Sheets

DIGITAL IMAGE MANAGEMENT SYSTEM HAVING METHOD FOR MANAGING IMAGES ACCORDING TO IMAGE GROUPS

FIELD OF THE INVENTION

This invention relates generally to the field of digital asset management, and more particularly to a digital image management system having a unique method for managing images as a single image group.

BACKGROUND

Modern hospitals have implemented networks of various digital modalities such as a magnetic resonance (MR), computed tomography (CT), digital radiography, and ultrasound devices. These modalities, referred to as input imaging devices, produce vast numbers of diagnostic quality digital medical images. In order to more easily manage such images many hospitals are implementing a network of specialized equipment and components designed to support medical radiological imaging commonly referred to as a Picture Archiving and Communicating System (PACS). A PACS allows a radiologist to easily manage the large volume of digital medical images including archiving, retrieving and displaying the images. For example, when a patient is imaged by a medical modality a series of digital images, referred to as a "study", is generated, captured and archived. A radiologists can easily retrieve the patient's study, or any previous study, and display the study on a display station for viewing. Furthermore, the retrieved study can be forwarded to another radiologist, perhaps located at a remote hospital. By easing the burden of managing digital medical images, PACS are expected to improve patient care and the efficiency of the radiology department. Furthermore, by integrating PACS with a Hospitals Information Management System (HIS), patient information can be coupled with the study, thereby improving the efficiency of the hospital as a whole.

In order to facilitate archival and fast retrieval of medical images, a PACS typically incorporates a short-term storage device having a plurality of short-term storage media, such as a jukebox of rewritable optical disks, and a long-term storage device having a plurality of long-term storage media, such as a tape archiving device capable of managing a library of tapes. As new images are generated from the various medical modalities, the system stores the images on the short-term storage device using a "best-fit" approach. In this manner, the system distributes the images across the plurality of short-term storage media in order to minimize wasted storage space. Thus, each image in a patient's study may be stored on a different medium in order to most efficiently manage storage space. A central database maintains the location of each image. If a radiologist does not request a patient's study for a period of time, the system automatically moves the corresponding images to the long-term storage device and updates the database. Again, the PACS distributes the images of the study across the long-term storage media within the long-term storage device to minimize wasted storage space. When, for example, a radiologist or a radiology technician (i.e., a user) requests a particular patient's study, the system accesses the database to determine the current location of the patient's images. If the desired images reside on long-term storage media within the long-term storage device, the PACS automatically retrieves the images and moves them to the short-term storage device. If some of the media is not currently within the long-term storage device, perhaps being physically moved to storage by a hospital personnel, the system requests the personnel to retrieve and insert all of the appropriate long-term storage media.

Although the best-fit archival scheme typically used by a PACS provides the benefits discussed above, it also has many shortcomings. For example, because the best-fit method distributes images across a plurality of media, it does not readily allow patient records to be physically archived to a shelf or an off-site storage facility. When a radiologist requests images for a particular patient, the hospital staff may have to physically retrieve several media from archive. Even if all the necessary long-term storage media is currently loaded into the long-term storage device, the device must independently initialize each long-term storage medium for access. Thus, in certain scenarios, the best-fit method can greatly increase archive retrieval time, thus compromising the efficiency of the archival system and increasing the cost thereof. For the reasons stated above, and for other reasons stated below which will become apparent to those skilled in the art upon reading and understanding the present specification, there is a need for a digital image management system which reduces access time and which requires less intervention by hospital personnel.

SUMMARY OF THE INVENTION

As explained in detail below, the present invention is directed to a method and system that facilitates image archival with a unique method for grouping customer image and information. As applied to medical environments, the system creates a "virtual film jacket" and manages medical images by modeling conventional hospital film archival procedures.

In one embodiment, the invention is a method for archiving a plurality of digital images associated with one of a plurality of customers. The method includes the step of selecting one of the customers and defining an image group to include all of the images associated with the selected customer. The image group is stored to a short-term storage device having a plurality of short-term storage media such that all of the images of the image group are maintained on a single short-term storage media. The customer image group is moved from the short-term storage device to a long-term storage device having a plurality of long-term storage media when the customer image group is not accessed by a user within a first predetermined period of time. In this manner, the long-term storage device stores the customer image group on a single long-term storage medium.

According one feature of the invention, a request is received from the user to store an input image associated with the selected customer and the database is accessed to read a location of the customer image group associated with the selected customer. Upon receiving the request, the customer image group associated with the selected customer is retrieved from the long-term storage device based on the location read from the database. Furthermore, the retrieved image group is moved to a single short-term storage medium within the short-term storage device. The input image is received from an input imaging device and stored on the short-term storage medium having the retrieved customer image group, thereby adding the received image to the retrieved customer image group.

According to another aspect of the invention, the image group is moved from the short-term storage device to a mid-term storage device when the image group is not accessed for a second predetermined period of time, wherein the mid-term storage device stores the image group on a single mid-term storage medium.

Another advantageous feature of the invention is that a user is automatically informed to physically retrieve a long-term storage medium from a storage facility when necessary and automatically informed to return the long-term storage medium to the storage facility when the image group is not accessed for a third predetermined period of time.

In one particularly beneficial embodiment, the customer is a patient and the input image is a medical diagnostic image produced by a medical modality. As such, the customer specific information includes at least one of the patient's name, a physician's name and a modality type for each image of the image group.

In another aspect, the invention is a digital information management system having an input imaging device for generating a plurality of images associated with one of a plurality of customers. The system further includes a short-term storage device, a long-term storage device, and a database maintaining an entry for each customer. A software system executes on a suitably configured computer and manages the plurality of images by selecting one of the customers, defining a customer image group to include all of the images associated with the selected customer, commanding a short-term storage device having a plurality of short-term storage media to store all of the images of the customer image group on a single short-term storage medium, and moving the customer image group from the short-term storage device to a long-term storage device having a plurality of long-term storage media when the customer image group is not accessed by a user within a first predetermined period of time. In this manner, the long-term storage device stores the images of the customer image group on a single long-term storage medium.

These and other features and advantages of the invention will become apparent from the following description of the preferred embodiments of the invention.

DETAILED DESCRIPTION

In the following detailed description, references are made to the accompanying drawings which illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

Figure 1:
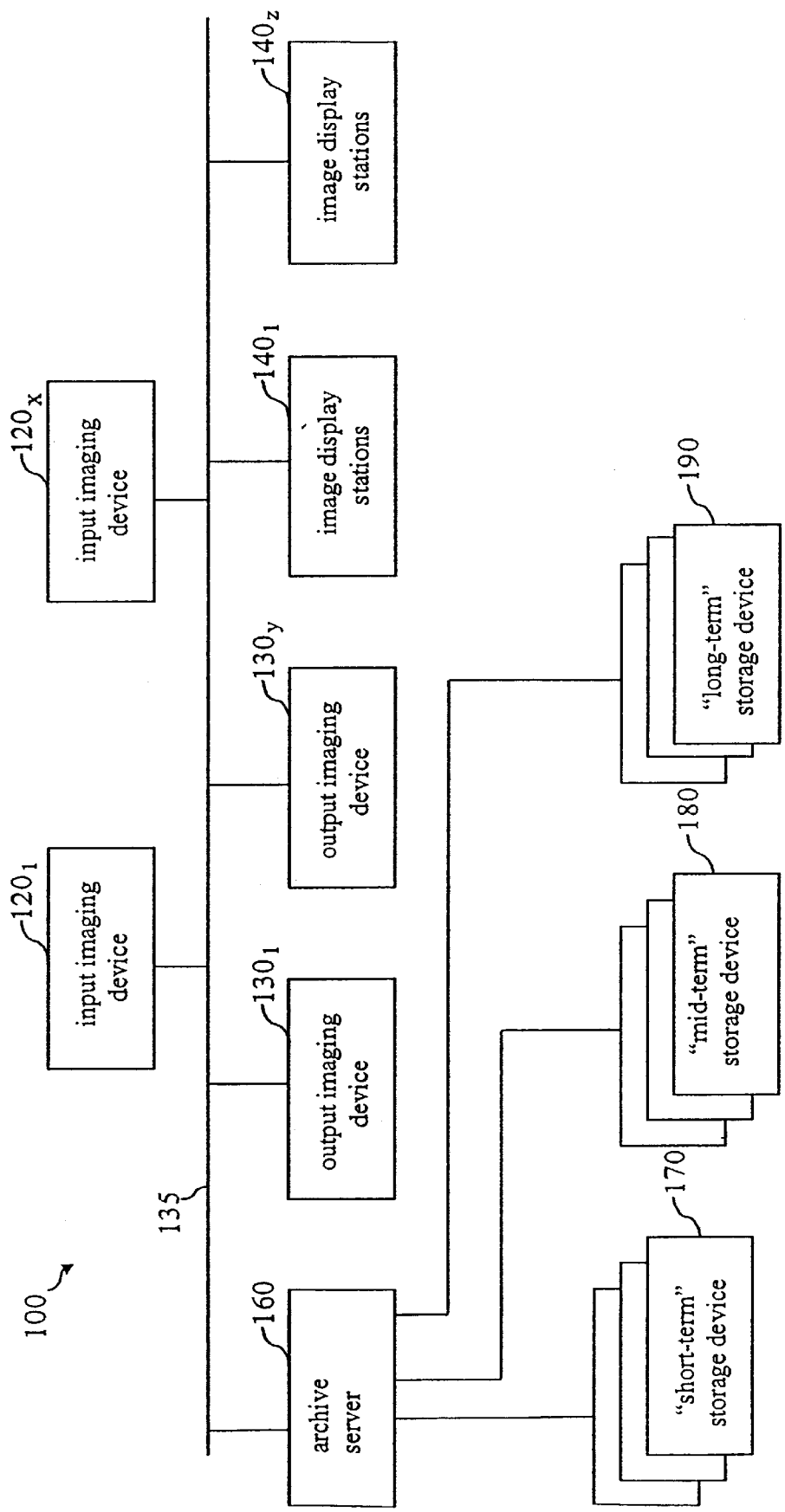
FIG. 1 illustrates one embodiment of a digital image management system in block diagram form having a plurality of input imaging devices, a plurality of image display stations, a plurality of output imaging devices and an archive server in accordance with the present invention.

FIG. 1 illustrates a digital image management system 100 in block diagram form. System 100 includes a plurality of input imaging devices 120, a plurality of output imaging devices 130, a plurality of image display stations 140 and archive server 160 communicatively interconnected via network 135. Each input imaging device 120 may be any image generating device capable of producing a digital image. For example, in a medical imaging environment input imaging devices 120 may be a variety of medical imaging modalities such as magnetic resonance (MR), computed tomography (CT), digital radiography, and ultrasound devices, manufactured by a number of different manufacturers, such as Siemens, Toshiba, GE, or Picker. The digital images produced by input imaging devices 120 are communicated via network 135 to output imaging devices 130, display stations 140 or archive manager 160. In addition to communicating the generated images, input imaging device 120 communicates customer specific information. For example, in the medical environment input imaging devices 120 may communicate a patient's name, a physician's name and a modality type. In one embodiment, images are communicated over network 135 using a data communications protocol developed by the American College of Radiology (ACR) and the National Electrical Manufacturers Association (NEMA) known as the DICOM protocol. The DICOM protocol is typically implemented using a TCP/IP connection between the communicating devices.

Archive server 160 archives each digital image received from network 135 according to the customer specific information associated with the image. Archive server 160 initially stores the received image on "short-term" storage device 170 for short-term storage. As discussed in detail below, archive server 160 manages "mid-term" storage device 180 and "long-term" storage device 190 by grouping customer images and information into a customer image group and maintaining the image group on a single storage medium such as a single diskette, optical disk, or tape. As applied to medical environments, archive server 160 models a hospital's film archival procedures by creating an image group, also referred to herein as a "virtual film jacket", and manipulating the images as a single group. In this manner, the image group contains all of the patient's previous studies. Archive server 160 manages a database (not shown) in order to maintain information about each image group including a location of each image. The present invention also contemplates a two-tier storage hierarchy having short-term storage device 170 and long-term storage device 190.

Upon request by a user, such as a radiologist or radiology technician, archive server 160 retrieves archived images from short-term storage device 170, mid-term storage device 180 and long-term storage device 190 and communicates the images to display stations 140 for viewing. In addition, archive server may communicate the retrieved images to output imaging devices 130 to produce a hardcopy output of the retrieved image. In a medical environment, output imaging devices 130 are continuous tone laser imagers for forming an image on an imaging element. In one embodiment, output imaging devices 130 include a processor station (not shown) for chemical processing and developing of the output image formed a photographic element. In another embodiment, the element is photothermographic and can be thermally processed and need not be chemically processed. Other imaging processes are also suitable for output imaging devices 130 including direct thermal imaging, ablation imaging, dye transfer, ink jet, dye sublimation and thermal mass transfer.

Figure 2:
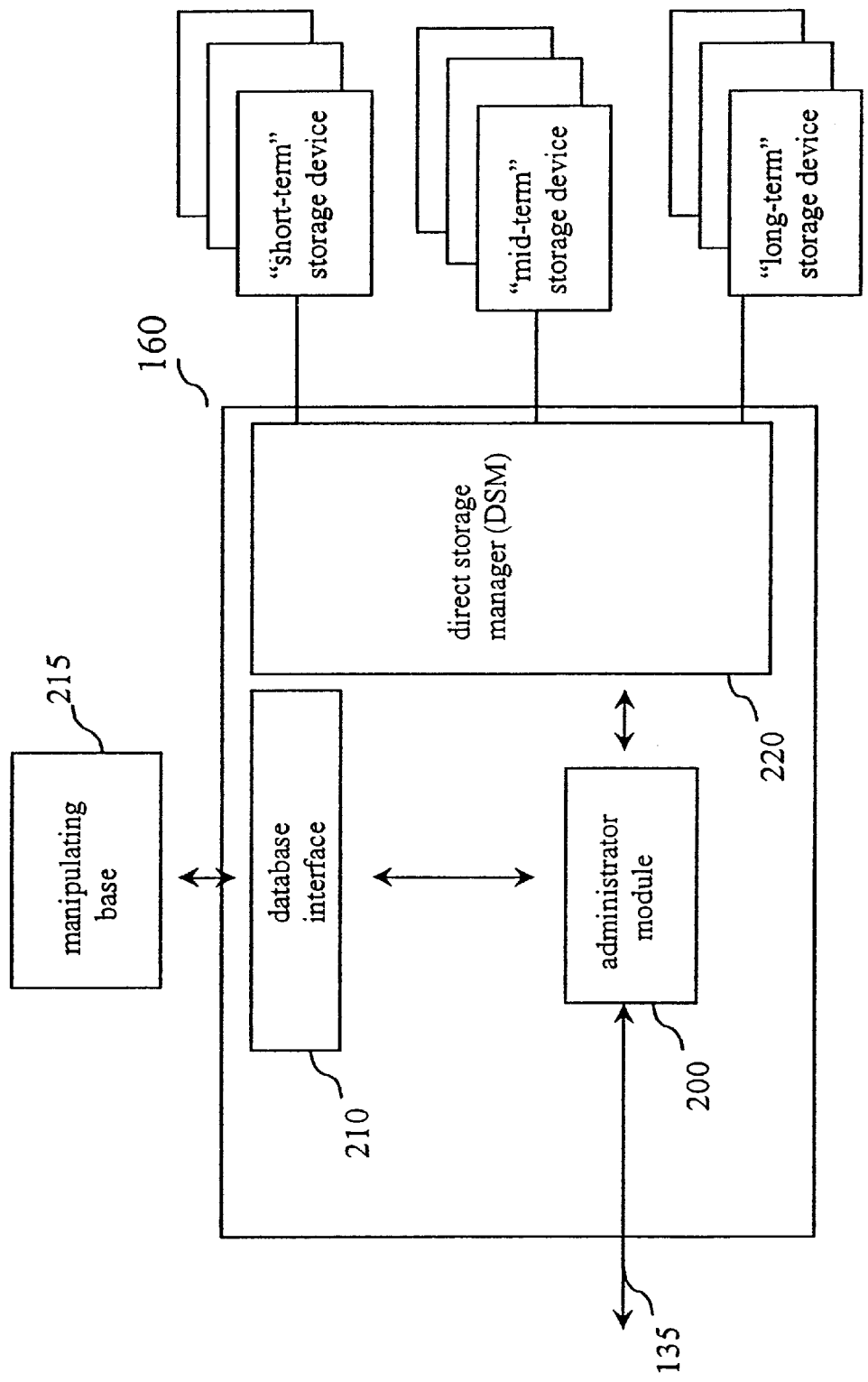
FIG. 2 illustrates one embodiment of the archive server of FIG. 1 implementing methods for clustering customer images as a single image group in accordance with the present invention.

FIG. 2 illustrates archive server 160 in block diagram form. Archive server 160 includes administrator module 200, database interface 210 for manipulating database 215, directed storage manager (DSM) 220 for controlling short-term storage device 170, mid-term storage device 180 and long-term storage device 190. Administration module 200 receives requests from network 135 and, based on these request, commands DSM 220 to either retrieve images from or store images to short-term storage device 170, mid-term storage device 180 and long-term storage device 190.

Figure 3:
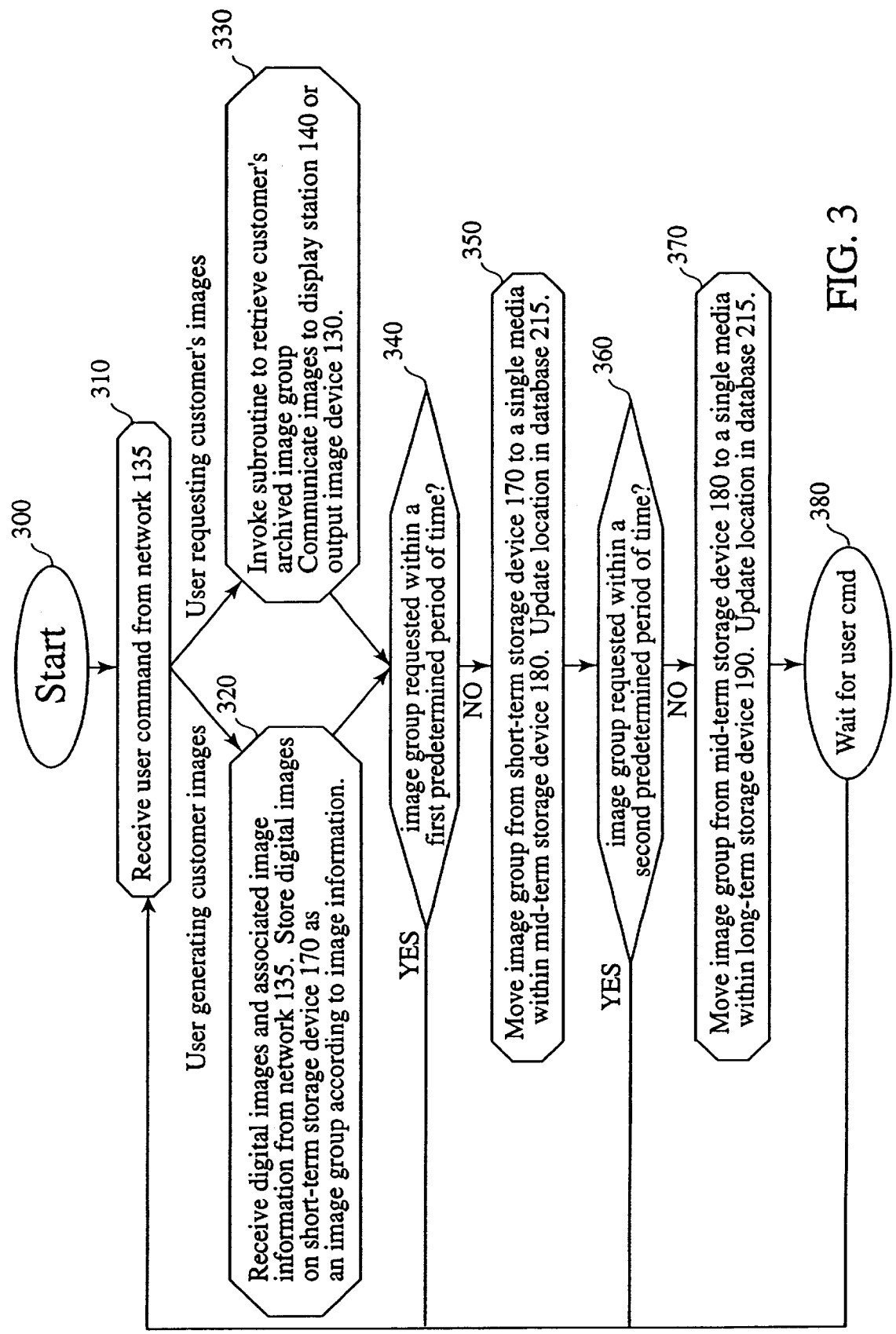
FIG. 3 is a flow chart illustrating one mode of operation of an archive server managing customer images as a single image group in accordance with the present invention.

FIG. 3 illustrate one mode of operation of administration module 200 of archive server 160. Referring to FIG. 3, administration module 200 begins execution at step 300 and proceeds to step 310 for receiving user commands from network 135. In one embodiment, administration module 200 receives user commands according to the DICOM protocol over a TCP/IP connection. Once administration module 200 receives a user command, administration module 200 determines whether the user wishes archive server 160 to store a plurality of images for a particular customer or whether the user wishes archive server 160 to retrieve archived images associated with a particular customer. For example, referring to FIG. 1, in a medical imaging environment a hospital personnel may generate a series of images by imaging a patient with a input imaging devices 120 which may be a MR, CT, digital radiography or ultrasound device. The hospital personnel directs input imaging device 120 to communicate the patient's study to archive server 160 and to command archive server 160 to store the corresponding images according to patient specific information. Additionally, hospital personnel may command archive server 135 to retrieve one or more studies of a particular patient and communicate the corresponding images to display station 140 for viewing. Similarly, hospital personnel may command archive server 165 to communicate the patient's study to output imaging device 130 for printing.

Referring again to FIG. 3, after receiving the user command in step 310, administration module 200 proceeds to either step 320 or step 330 depending on whether the user wishes to store a series of new images or wishes to retrieve images for a particular customer, respectively.

Figure 4:
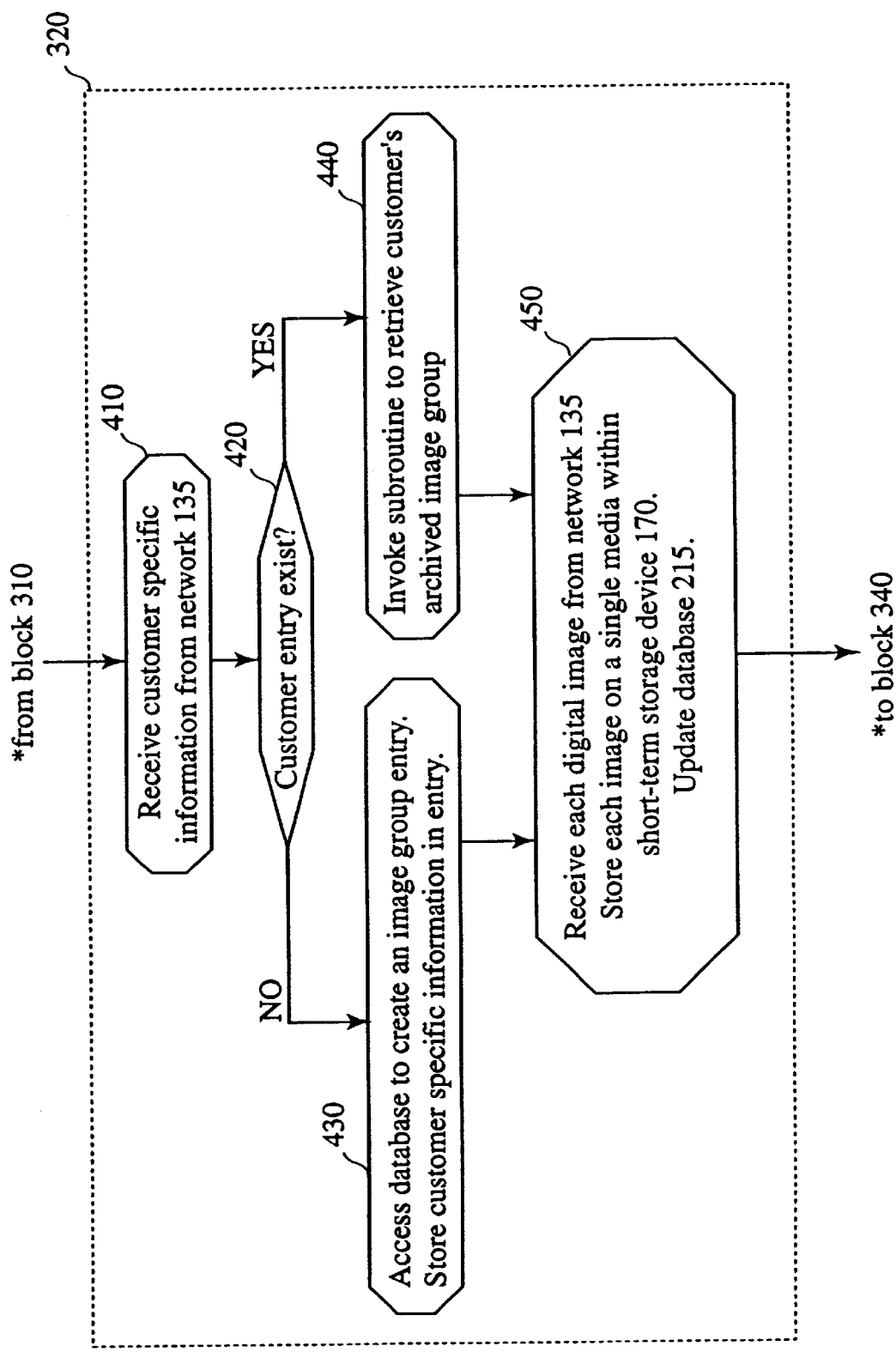
FIG. 4 details a portion of the flow chart of FIG. 3 in which the archive server receives digital images and creates an image group.

FIG. 4 illustrates step 320 in detail. Referring to FIG. 4, administration module 200 proceeds to step 410 and receives customer specific information from network 135. In step 420, administration module 200 access database 215 via database interface 210 and determines whether an entry for the customer already exists. If an entry does not exist, administration module 200 proceeds to step 430 and commands database interface 210 to create an entry for the customer in database 215. Upon creating an entry, administration module 200 stores the customer specific information in the new entry and proceeds to step 450. If an entry already exists, the administration module 200 proceeds from step 420 to step 440 and invokes the subroutine illustrated in FIG. 5 to retrieve a customer's entire image group.

Figure 5:
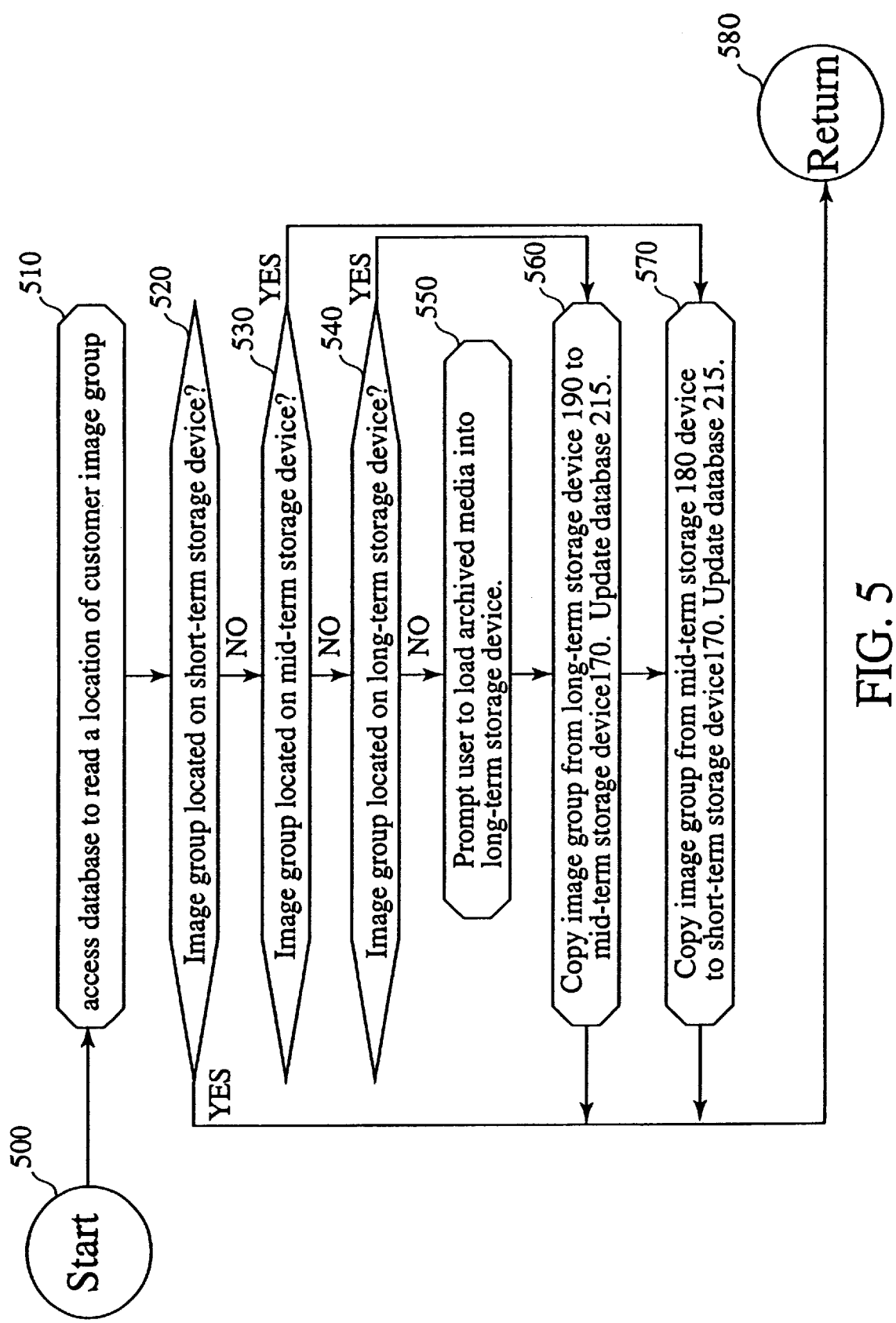
FIG. 5 is a flow chart illustrating a subroutine invoked by the flow chart of FIG. 3 to retrieve an archived image group.

The image group retrieval subroutine of FIG. 5 retrieves all of the images associated with a particular customer. In the medical imaging arena, the subroutine retrieves all of studies associated with a particular patient. Thus, according to one feature of the invention, every images associated with a customer resides on a single storage medium within short-term storage device 170, mid-term storage device 180 or long-term storage device 190. As described above, this cluster of images and customer specific information shall be referred to as an image group or, with regards to the medical environment, as a virtual film jacket.

Referring to FIG. 5, administration module 200 begins execution of the image group retrieval subroutine at step 500, immediately proceeds to step 510 and accesses database 215 to read the location of the customer's image group. In step 520, the administration module 200 tests whether the image group is located on short-term storage device 170. If the test is satisfied, administration module 200 proceeds immediately to ending step 580 since the image group need not be retrieved from archive. If the test fails, administration module 200 proceeds to step 530 and test whether the image group is located on mid-term storage device 180. If the test is satisfied, administration module 200 jumps to step 570 and moves the image group from a single mid-term storage medium within the mid-term storage device 180 to short-term storage device 170 and exits via step 580. If the test fails, administration module 200 proceeds to step 540 and test whether the customer's image group is located on a long-term storage medium located within long-term storage device 190. If the test is satisfied, administration module 200 jumps to step 560 and moves the image group from the long-term storage medium within the long-term storage device 190 to a single short-term storage medium within short-term storage device 170 and exits via step 580. A failure of this test indicates that the long-term storage medium on which the customer's image group resides has been removed from long-term storage device 190 and has been physically archived to a shelf or warehouse. Thus, if the test fails, administration module 200 proceeds to step 550 and prompts a user to retrieve the long-term storage medium and insert it into long-term storage device 190. After the long-term storage medium has been physically retrieved by hospital personnel, administration module 200 proceeds to step 560, moves the image group from the newly inserted long-term storage medium to a single short-term storage medium within short-term storage device 170 and exits via step 580.

Referring again to FIG. 4, after retrieving the customer's image group in step 440, administration module 200 proceeds to step 450. In step 450, administration module 200 receives each digital image from network 135 and stores the image on a single short-term storage medium within short-term storage device 170. If a new customer entry was created in step 430, the administration module 200 stores the images on any single short-term storage medium within short-term storage device 170 having space sufficient to hold the entire image group. If an image group for the customer has been retrieved via step 440 then administration module 200 stores the new images on the short-term storage medium within short-term storage device 170 that holds the customer's image group. If the short-term storage medium does not have sufficient room to store the images, then administration module 200 moves the existing image group to a new short-term storage medium within short-term storage device 170 and stores the received images upon the new short-term storage medium. If necessary, administration module 200 prompts the user to insert a blank short-term storage medium for short-term storage device 170. In this manner, archive server 160 maintains a customer image group comprising all of a customer's images on a single short-term storage medium within short-term storage device 170. After storing the newly generated images, administration module 200 returns from step 450 of FIG. 4 to step 340 of FIG. 3.

Referring again to FIG. 3, if the user wishes to retrieve images for a particular customer administration module 200 does not proceed from step 310 to step 320 as described above but rather proceeds to step 330. In step 330, administration module 200 retrieves the customer's image group by invoking the image group retrieval routine illustrated in FIG. 5 as described above. After retrieving a customer's image group, administration module 200 communicates the corresponding images to display station 140 or output imaging device 130 according to the user command. For example, in a medical environment a radiologist may wish to review images that were generated during a patient's exam. Upon receiving a request for a patient's image group, administration module 200 retrieves the images as described above and communicates them to display station 140 for review by the radiologist. Similarly, administration module 200 can readily communicate the images of the retrieved image group to output imaging device 130 for producing an output image on an imaging element.

Referring again to FIG. 3, once an image group has been stored or retrieved from archive and resides on short-term storage device 170, administration module 200 manages the image group such that all of the images are maintained on a single short-term storage medium. Thus, in step 340 administration module 200 tests whether the image group has been requested within a first period of time. If the image group is requested, administration module 200 returns to step 310 and processes the request as described above. If the image group is not requested within the first period of time, administration module 200 proceeds to step 350 and archives the entire image group by moving the image group from short-term storage device 170 to a single mid-term storage medium within mid-term storage device 180. If mid-term storage device does not contain a mid-term storage medium with sufficient room to hold the image group, administration module 200 requests the user to insert a blank mid-term storage medium. The first predetermined period of time is preferably configurable by the user and, in one embodiment, is preset to one week.

Upon moving the image group, administration module 200 updates the location of the image group within database 215 and proceeds to step 360. In step 360 administration module 200 test whether the image group has been requested within a second period of time. If the image group is requested, then administration module 200 returns to step 310 and processes the request as described above. If the image group is not requested within the second period of time, administration module 200 proceeds to step 370 and archives the entire image group by moving the image group from mid-term storage device 170 to a single long-term storage medium within long-term storage device 180. If long-term storage device does not contain a long-term storage medium having sufficient room to hold the image group, administration module 200 requests the user to insert a blank long-term storage medium. The second predetermined period of time is preferably configurable by the user and, in one embodiment, the second period of time is preset to six months.

Upon moving the image group to long-term storage device 190, administration module 200 proceeds to step 380 and waits for user commands. Upon receiving a user command, administration module 200 jumps to step 310 and processes the command. In one embodiment, not illustrated by FIG. 3, in step 380 administration module 200 tests whether the image group is requested within a third period of time. If the image group is not requested within the third time period, administration module 200 prompts the user to physically remove from long-term storage device 190 the long-term storage medium storing the image group and to physically archive the medium to a shelf or a warehouse.

Various embodiments of a digital image management system having a unique method for managing a customer images have been described. In one embodiment, the digital management system includes a plurality of input imaging devices, a plurality of image display stations, a plurality of output imaging devices and archive server communicatively interconnected via a network. In another embodiment, the digital image management system is a PACS system for easily managing the great volumes of digital medical images produces by a variety of medical imaging modalities such as MR, CT, digital radiography, and ultrasound devices. In another embodiment, the digital image management system readily manages consumer images such as scanned photographs, scanned negatives and digitized video clips. Furthermore, the inventive method for managing customer images is easily applicable to managing customer specific information. For example, in a medical environment, the digital image management system described herein can cluster patient images with other patient records including medical history, financial and personal information.

Several advantages of the present invention have been illustrated including minimizing access time since only a single storage medium need be retrieved and initialized before accessing customer information. Furthermore, the present invention readily allows customer images to be physically archived to a shelf or an off-site storage facility. Additionally, the present invention is easy for users, such as hospital personnel, to understand and thereby more effectively manage their archives. The term "user" can further apply to a subsystem which is designed to automate steps within the storage, retrieval and display process.

This application is intended to cover any adaptations or variations of the present invention. It is manifestly intended that this invention be limited only by the claims and equivalents thereof.

We claim:

1. A method for archiving a plurality of digital images, wherein each image is associated with one of a plurality of customers, the method comprising the steps of:

selecting one of the customers;

defining an image group to include all of the images associated with the selected customer;

storing the image group to a short-term storage device having a plurality of individually removable short-term storage media such that all of the images of the image group are maintained on a single short-term storage media;

moving the customer image group from said short-term storage device to a mid-term storage device having a plurality of individually removable mid-term storage media when the customer image group is not accessed by a user within a first predetermined period of time, wherein the mid-term storage device stores the customer image group on a single mid-term storage medium; and moving the customer image group from the mid-term storage device to a long-term storage device having a plurality of individually removable long-term storage media when the customer image group is not accessed by a user within a second predetermined period of time, wherein the long-term storage device stores the customer image group on a single long-term storage medium.

2. The method of claim 1, wherein the storing step comprises the steps of:

receiving a request from the user to store an input image associated with the selected customer;

accessing the database to read a location of the customer image group associated with the selected customer;

retrieving the customer image group associated with the selected customer from the long-term storage device based on the location read from the database, wherein the retrieved image group is moved to a single short-term storage medium within the short-term storage device;

receiving the input image from an input imaging device; and storing the received input image on the short-term storage medium having the retrieved customer image group, thereby adding the received image to the retrieved customer image group.

3. The method of claim 1, wherein the short-term storage device is a redundant array of independent disks.

4. The method of claim 1, wherein the mid-term storage device is a magneto-optical storage device.

5. The method of claim 1, wherein the long-term storage device is selected from one of 4 mm tape drive, 8 mm tape drive, and 9-track tape drive.

6. The method of claim 1, wherein the long-term storage device is a digital linear tape device holding a plurality of tapes.

7. The method of claim 2, wherein the retrieving step further comprises the steps of automatically informing a user to physically retrieve a long-term storage medium from a storage facility, and automatically informing the user to physically return the long-term storage medium to the storage facility when the image group is not accessed for a third predetermined period of time.

8. The method of claim 2, wherein the customer is a patient and the received input image is a medical diagnostic image produced by a medical modality.

9. The method of claim 2, wherein the received input image is generated by scanning a photograph.

10. The method of claim 2, wherein the received input image is generated by scanning a negative.

11. The method of claim 2, wherein the received input image is a digitized movie generated by digitizing information stored on a VHS tape.

12. The method of claim 2, wherein the customer image group further includes customer specific information other then the images associated with the customer.

13. The method of claim 12, wherein the customer is a patient and the input image is a medical diagnostic image produced by a medical modality, and further wherein the customer specific information includes at least one of the patient's name, a physician's name and a modality type for each image of the image group.

14. A digital information management system comprising:

an input imaging device for generating a plurality of images, wherein each image is associated with one of a plurality of customers;

a short-term storage device;

a mid-term storage device;

a long-term storage device;

a database maintaining an entry for each customer; and a software system executing on a suitably configured computer for managing the plurality of images by performing the steps of:
  selecting one of the customers;
  defining a customer image group to include all of the images associated with the selected customer;
  commanding a short-term storage device having a plurality of individually removable short-term storage media to store all of the images of the customer image group on a single short-term storage medium;
  moving the customer image group from said short-term storage device to a mid-term storage device having a plurality of individually removable mid-term storage media when the customer image group is not accessed by a user within first predetermined period of time, wherein the mid-term storage device stores the customer image group on a single mid-term storage medium; and
  moving the customer image group from the short-term storage device to a long-term storage device having a plurality of individually removable long-term storage media when the customer image group is not accessed by a user within a second predetermined period of time, wherein the long-term storage device stores the images of the customer image group on a single long-term storage medium.

15. The digital information management system of claim 14, wherein the commanding step of the software program comprises the steps of:

receiving a request from the user to store an input image associated with the selected customer;

accessing the database to read a location of the customer image group associated with the selected customer;

retrieving the customer image group associated with the selected customer from the long-term storage device based on the location read from the database, wherein the retrieved image group is moved to a single short-term storage medium within the short-term storage device;

receiving the input image from an input imaging device; and storing the received input image on the short-term storage medium having the retrieved customer image group, thereby adding the received image to the retrieved customer image group.

16. The digital information management system of claim 14, wherein the short-term storage device is a redundant array of independent disks.

17. The digital information management system of claim 14, wherein the mid-term storage device is a magneto-optical storage device.

18. The digital information management system of claim 14, wherein the long-term storage device is selected from one of 4 mm tape drive, 8 mm tape drive, and 9-track tape drive.

19. The digital information management system of claim 15, wherein the long-term storage device is a digital linear tape device holding a plurality of tapes.

20. The digital information management system of claim 19, wherein the software system automatically informs a user to physically retrieve a tape from a tape archive, and further wherein the moving step further comprises the step of automatically informing the user to physically return the tape to the archive.

21. The digital information management system of claim 14, wherein the customer is a patient and the input imaging device is a medical modality that produces medical diagnostic images.

22. The digital information management system of claim 15, wherein the input imaging device produces an input image by scanning a photograph.

23. The digital information management system of claim 15, wherein the input imaging device produces an input image by scanning a negative.

24. The digital information management system of claim 15, wherein the input image is a digitized movie and wherein the input image device produces an input image by digitizing information stored on a VHS tape.

* * * * *